(12) United States Patent
Lustig et al.

(10) Patent No.: US 6,358,052 B1
(45) Date of Patent: Mar. 19, 2002

(54) DENTAL IMPLANT SYSTEM AND METHOD FOR EFFECTING A DENTAL RESTORATION USING THE SAME

(76) Inventors: L. Paul Lustig, 304 Greenwood St., Newton, MA (US) 02159; Federico Castellucci, 719 South Ave., Weston, MA (US) 02193; Andrew P. Tybinkowski, 39 Burning Bush Dr., Boxford, MA (US) 01921

( * ) Notice: Subject to any disclaimer, the term of this patent is extended or adjusted under 35 U.S.C. 154(b) by 0 days.

(21) Appl. No.: 09/354,393

(22) Filed: Jul. 15, 1999

(51) Int. Cl.[7] .................................................. A61C 8/00
(52) U.S. Cl. ...................................................... 433/174
(58) Field of Search ................. 433/173, 174, 433/175, 176

(56) References Cited

U.S. PATENT DOCUMENTS

| | | | | |
|---|---|---|---|---|
| 4,854,872 A | * | 8/1989 | Detsch | 433/174 |
| 5,071,350 A | * | 12/1991 | Niznick | 433/173 |
| 5,073,110 A | * | 12/1991 | Barbone | 433/173 |
| 5,145,371 A | * | 9/1992 | Jorneus | 433/174 |
| 5,178,539 A | * | 1/1993 | Peltier et al. | 433/173 |
| 5,302,125 A | * | 4/1994 | Kownacki et al. | 433/173 |
| 5,662,476 A | * | 9/1997 | Ingber et al. | 43/173 |
| 5,755,574 A | * | 5/1998 | D'Alise | 433/173 |
| 5,762,500 A | * | 6/1998 | Lazarof | 433/173 |
| 5,904,483 A | * | 5/1999 | Wade | 433/173 |

* cited by examiner

Primary Examiner—Todd E. Manahan
(74) Attorney, Agent, or Firm—Pandiscio & Pandiscio

(57) ABSTRACT

A dental implant system and method for effecting a dental restoration using the same. The dental implant system having an implant fixture adapted to be deployed in a bone; an impression coping adapted to be selectively deployed on the implant fixture and in a dental impression; a laboratory analog adapted to be selectively deployed on the impression coping and in a dental cast; a spherical abutment adapted to be selectively deployed on the laboratory analog; and a multiaxis abutment adapted to be adjustably deployed on the spherical abutment; wherein the spherical abutment and the multiaxis abutment are used to generate a cast permanent abutment which may be received by the laboratory analog and the implant fixture.

25 Claims, 16 Drawing Sheets

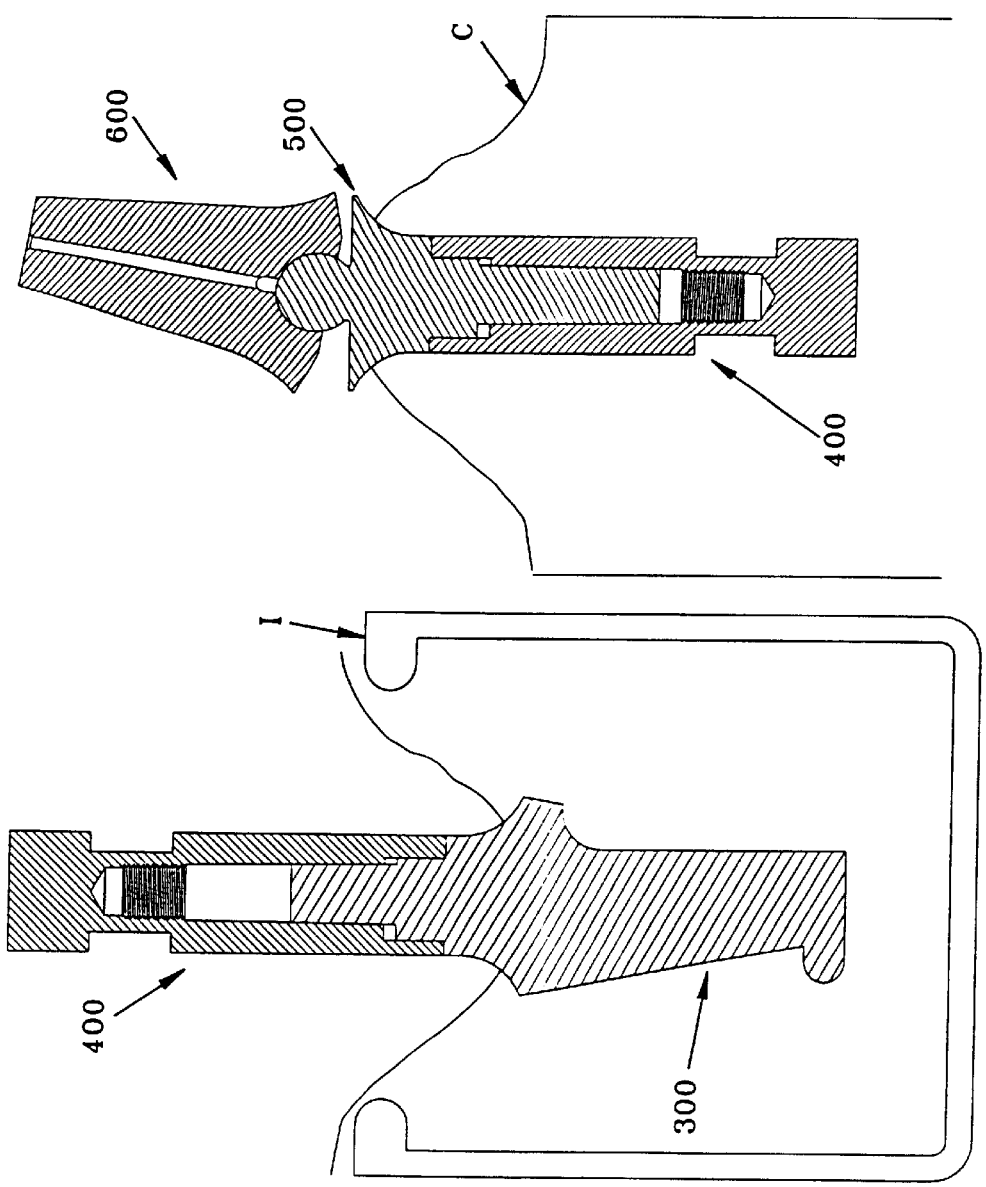

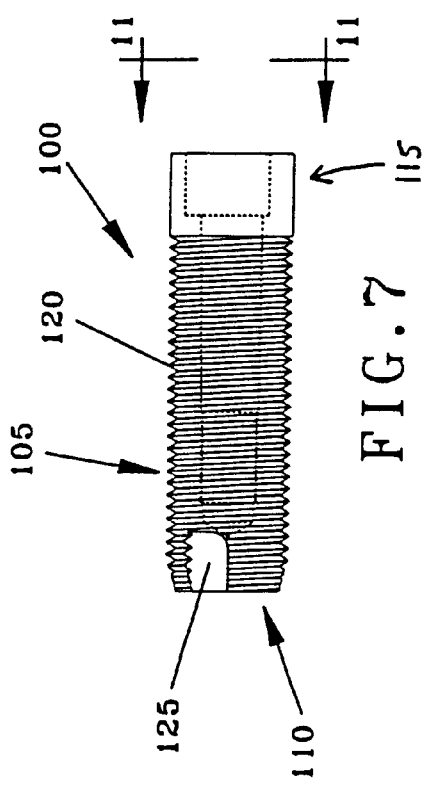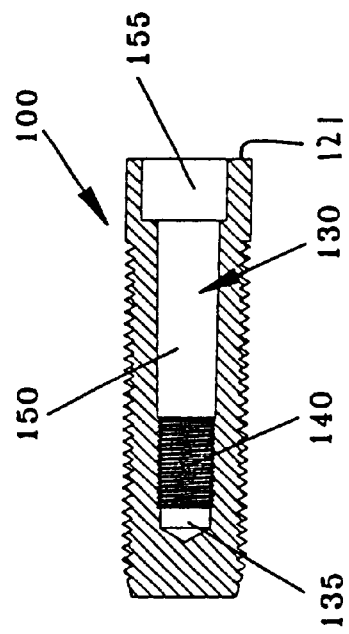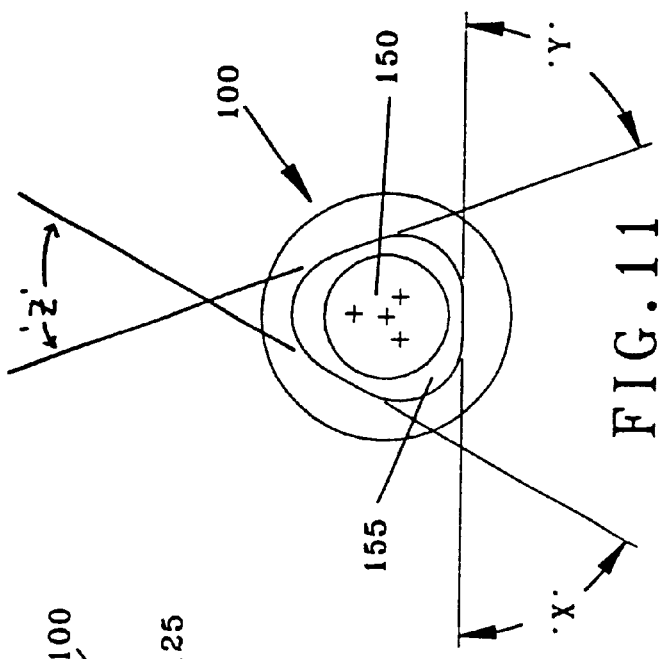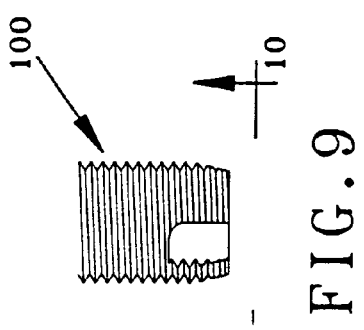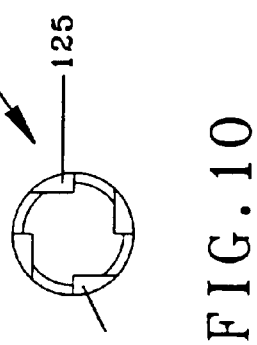

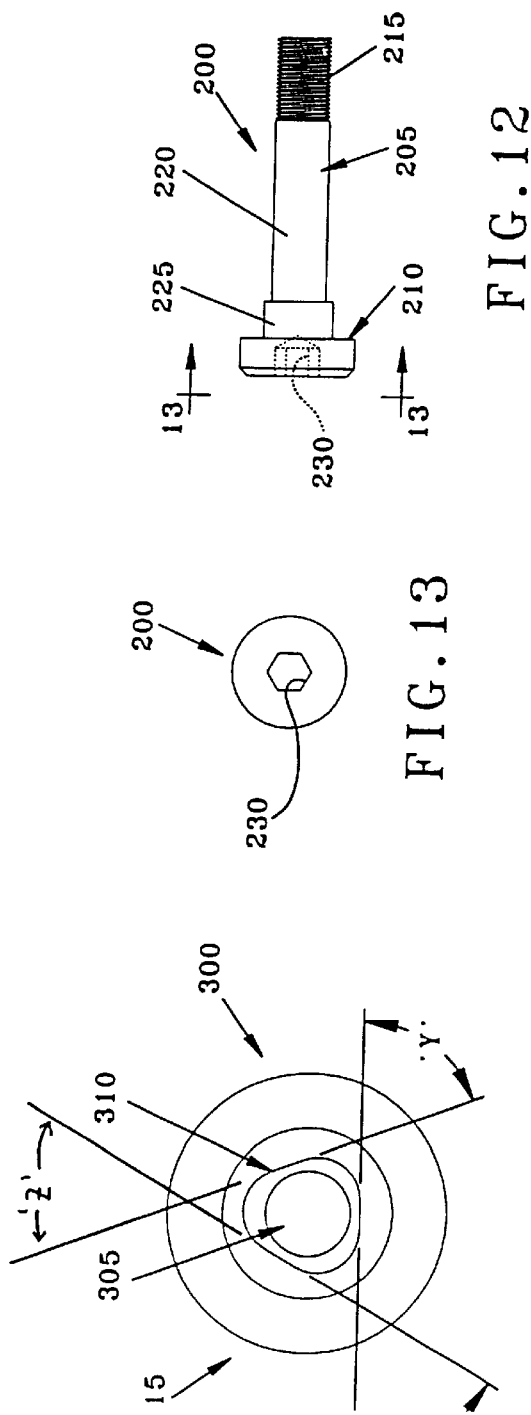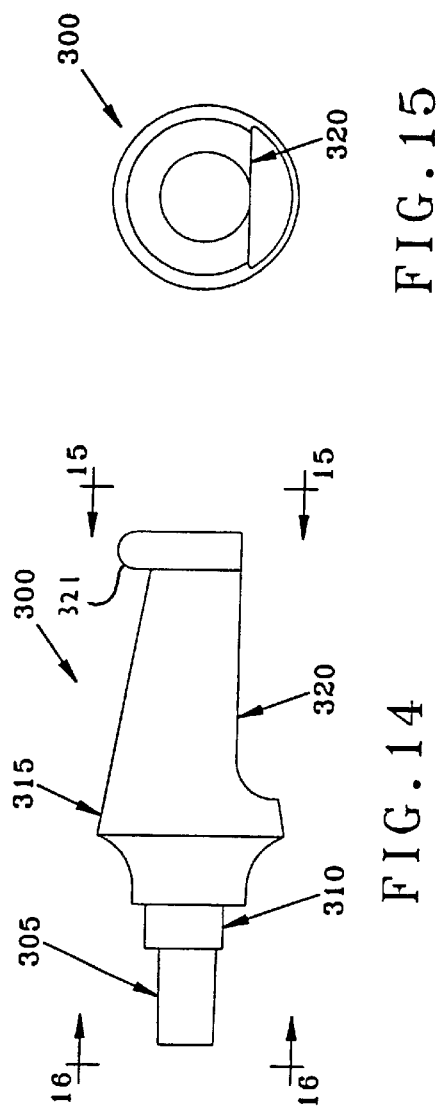

SCALE 2/1

SCALE 2/1

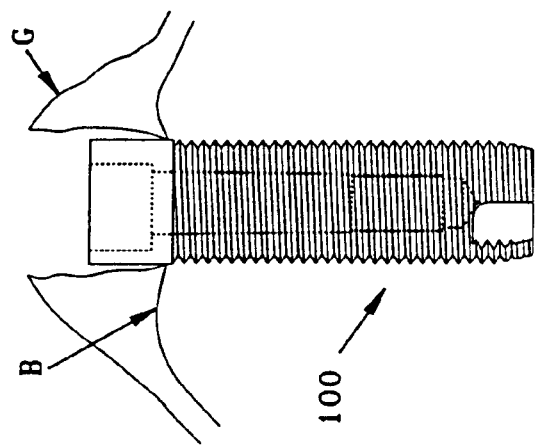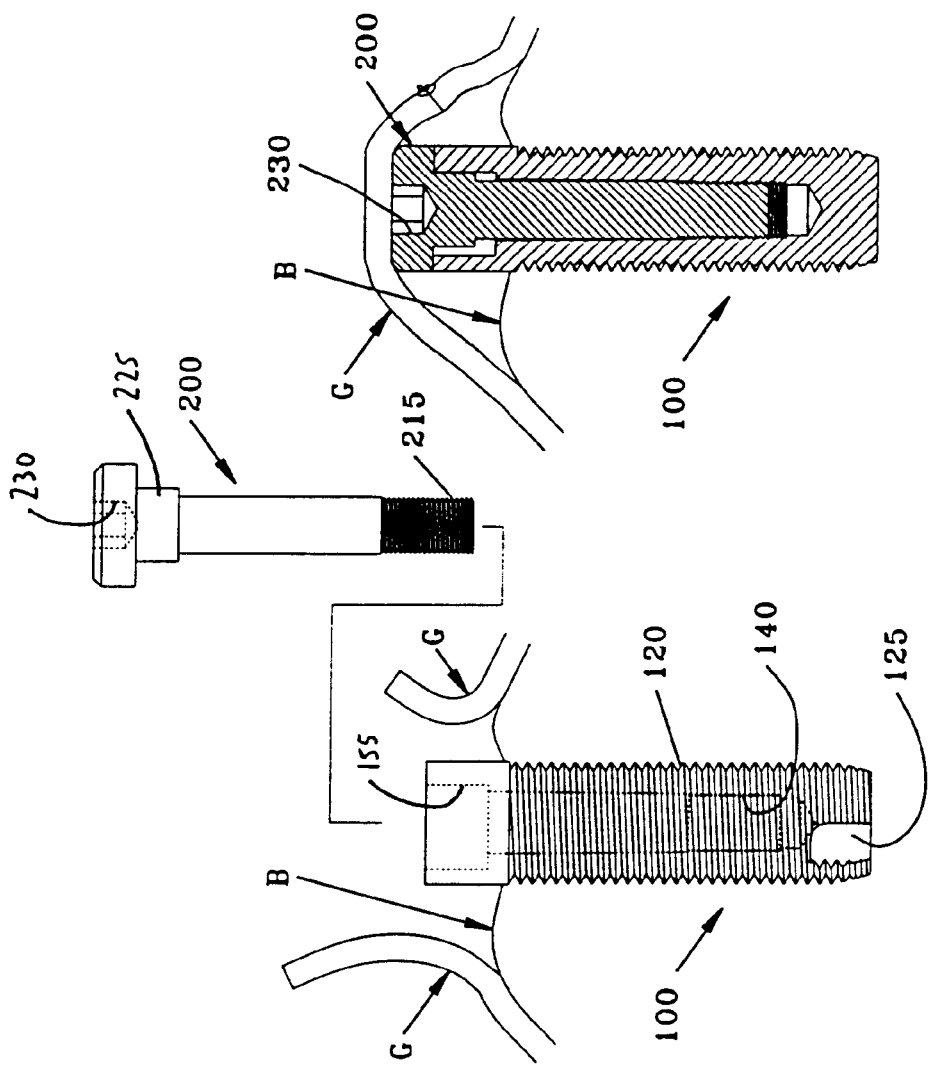
FIG. 29
FIG. 28
FIG. 27

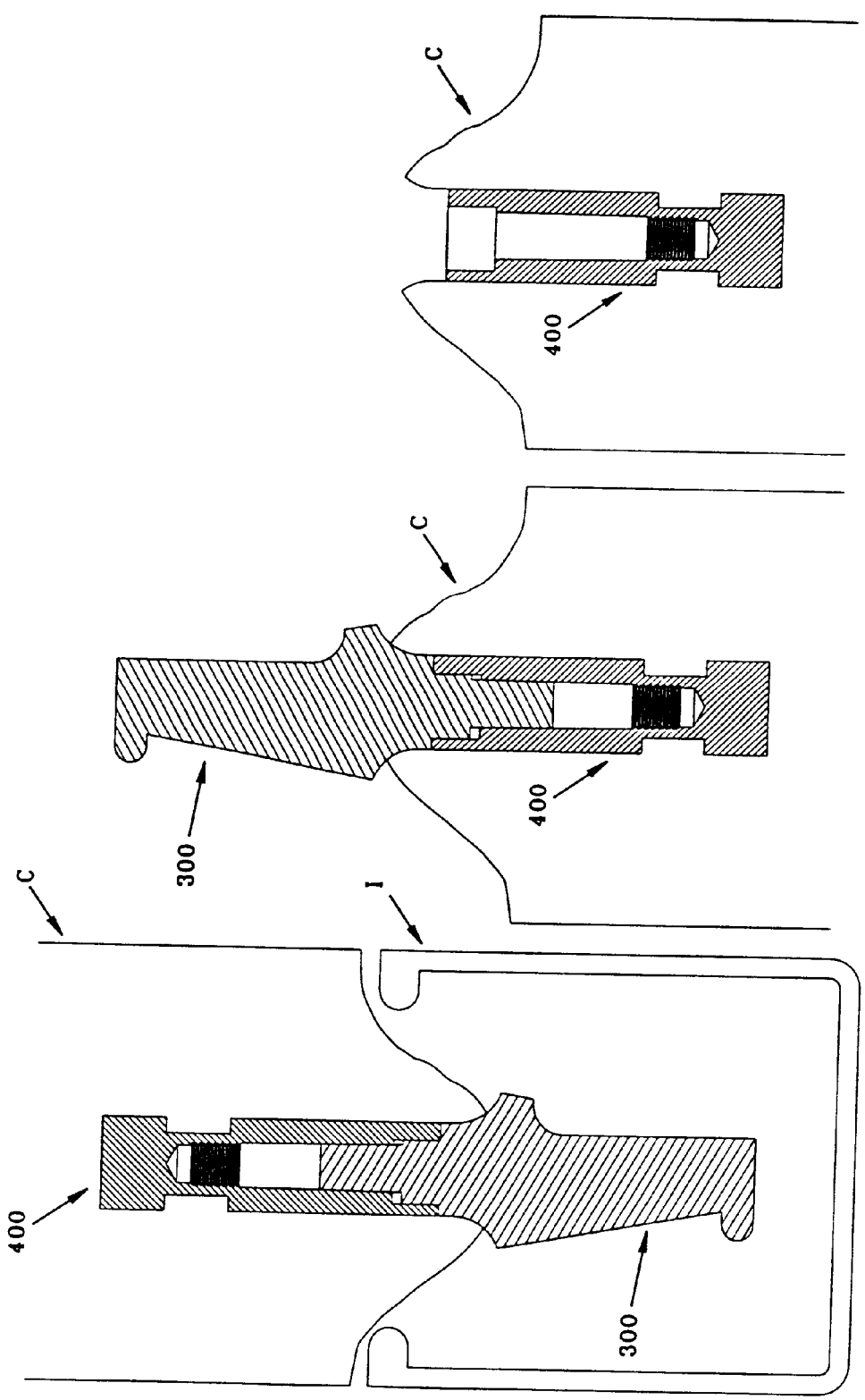

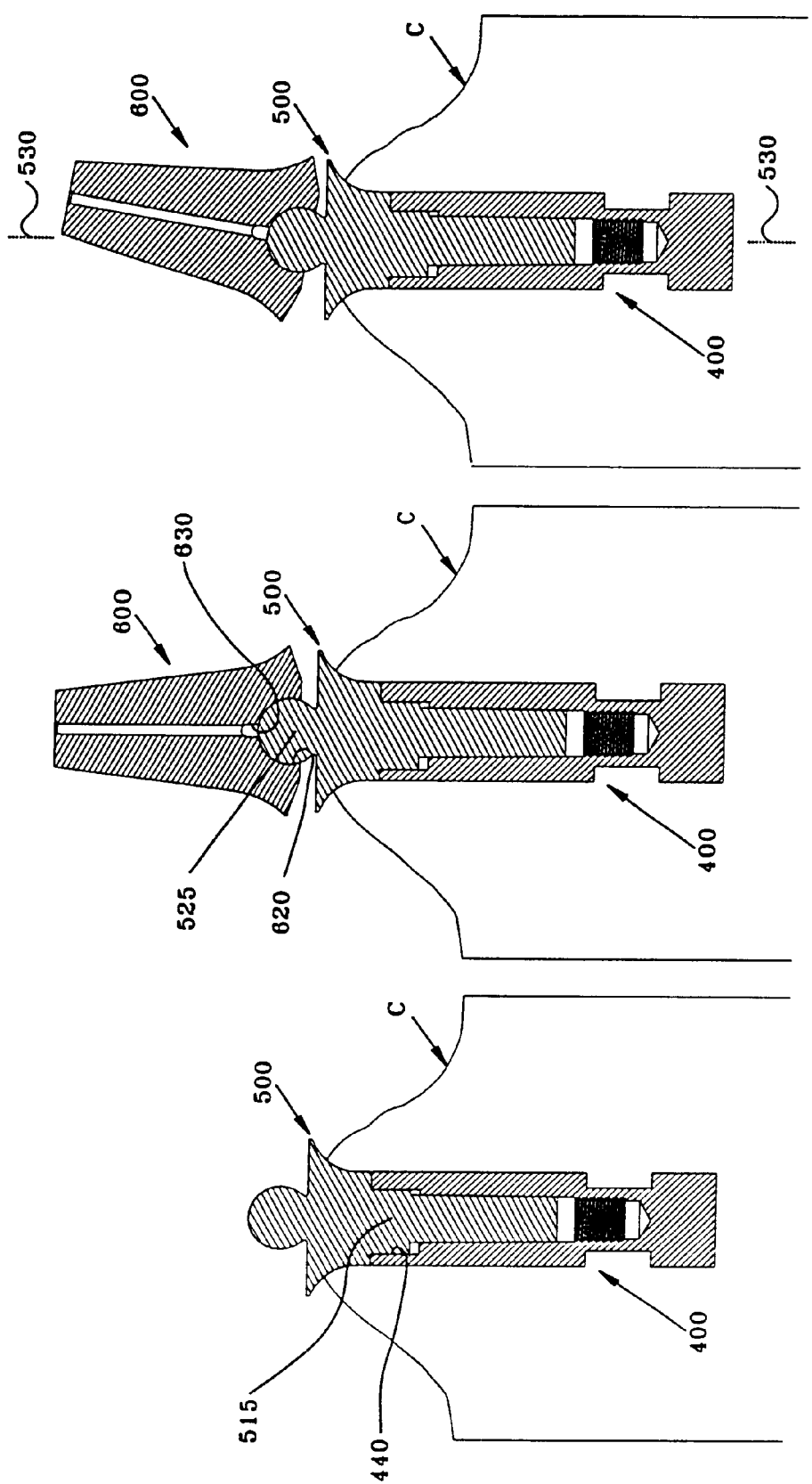

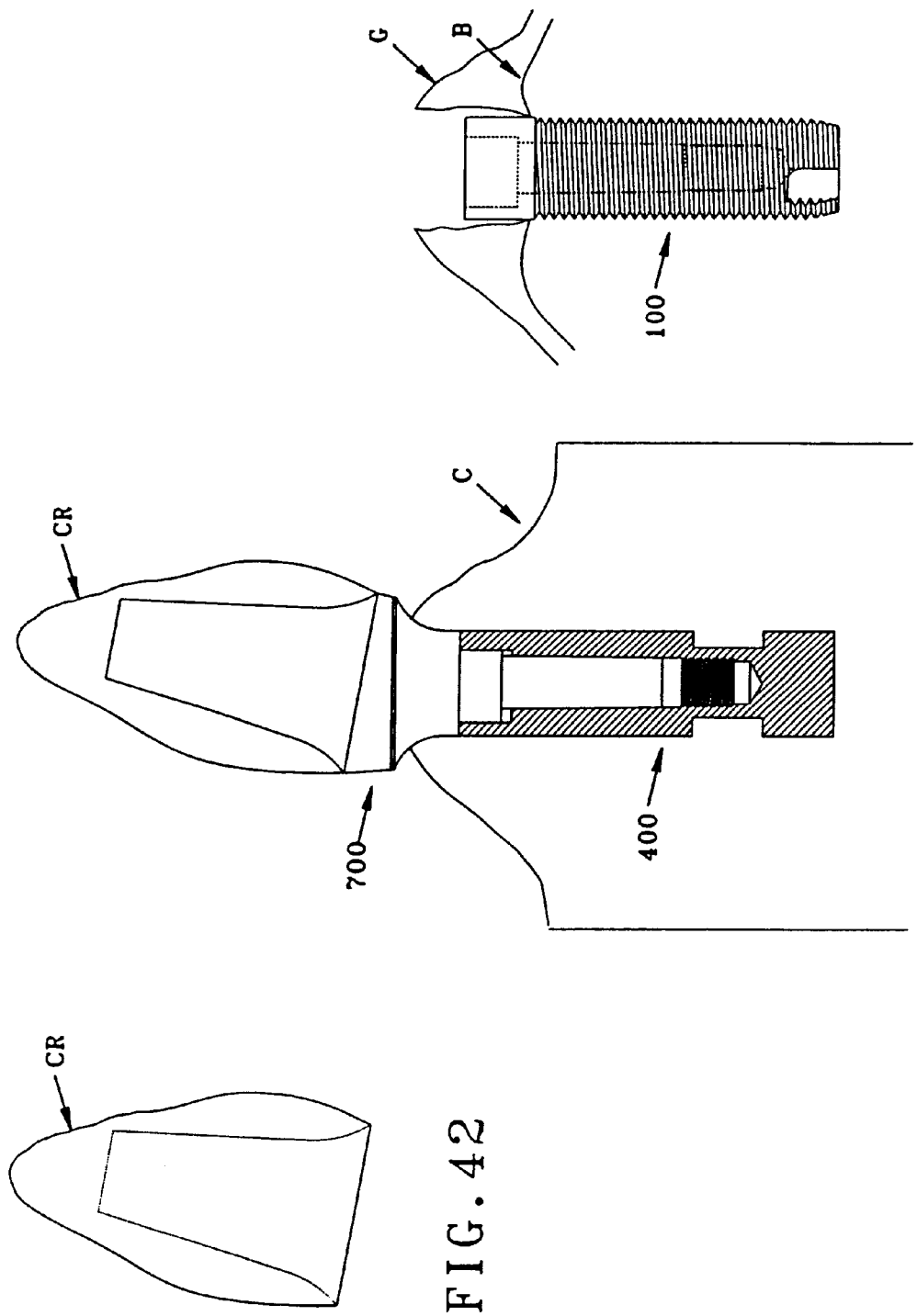

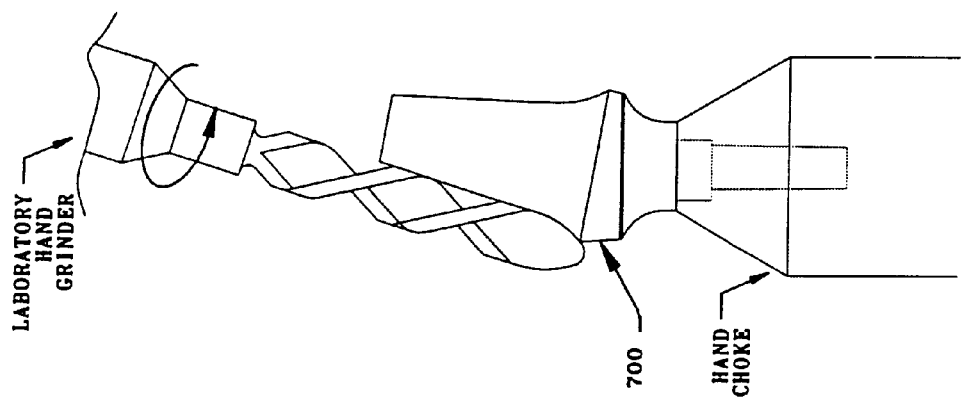
FIG. 50
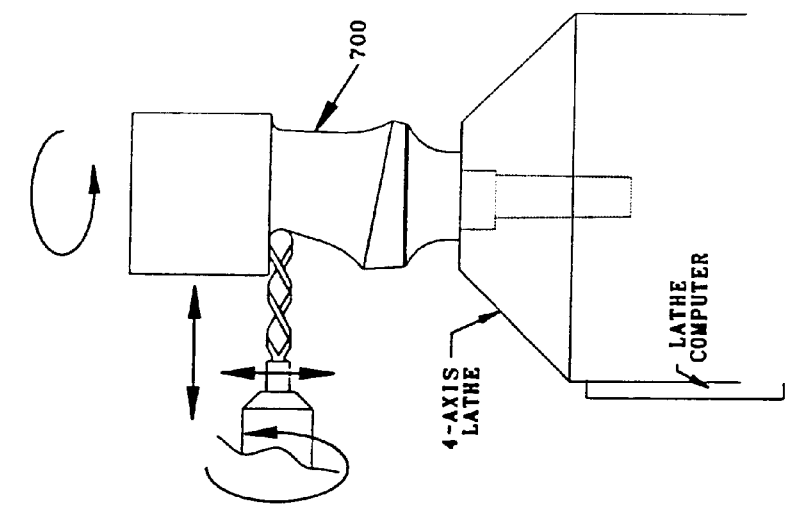
FIG. 49
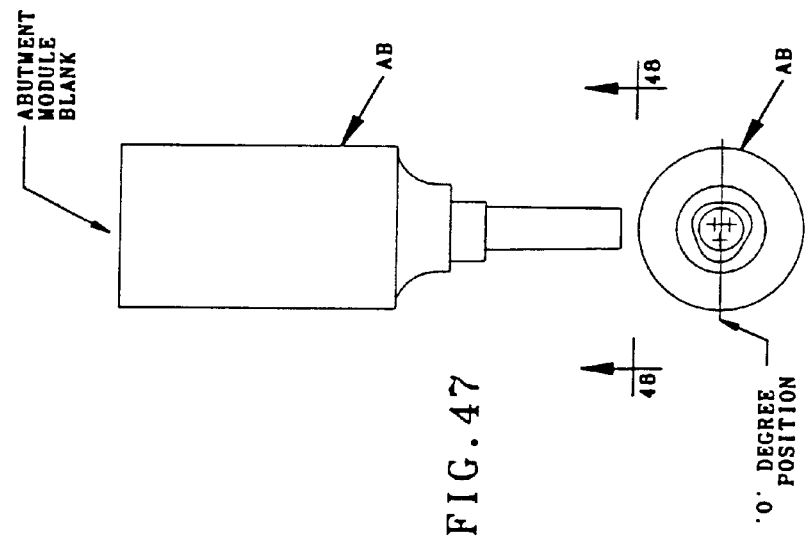
FIG. 47
FIG. 48

DENTAL IMPLANT SYSTEM AND METHOD FOR EFFECTING A DENTAL RESTORATION USING THE SAME

FIELD OF THE INVENTION

This invention relates to dental apparatus and procedures in general, and more particularly to dental implant systems and methods for effecting dental restorations using the same.

BACKGROUND OF THE INVENTION

In many individuals, disease and/or injury may result in the loss of one or more natural teeth. As a result, various techniques have been developed to replace such lost natural teeth with prosthetic appliances.

For example, where sufficient natural teeth remain adjacent to the location where a prosthetic tooth is to be positioned, a bridge may be fabricated.

Alternatively, if insufficient natural teeth remain to support and stabilize a bridge, a denture may be fabricated, with the denture seating against the patient's gingiva.

In still other situations, a dental implant may be used. With such a dental implant, a hole is generally first made in the upper or lower jaw bone, as appropriate, and then the distal end of the implant is fixed in the recipient bone. e.g., by screwing the implant into the bone. The dental implant is generally sized and positioned so that the proximal end of the implant protrudes at least partially into the space where the prosthetic tooth is to be positioned. Then the prosthetic tooth is fixed to the proximal end of the implant, such that the prosthetic tooth generally occupies the space of the lost tooth.

While such dental implants can be effective, they also tend to suffer from a number of problems. Among other things, with current dental implants, the longitudinal axis of the prosthetic tooth must generally follow the longitudinal axis of the implant which is seated in the bone. Unfortunately, the optimal axial alignment for the implant seated in the bone may not necessarily be the same as the optimal axial alignment for the prosthetic tooth extending into the mouth. In particular, it has been found that the optimal axial alignment for the implant tends to be dictated by the specific anatomy of the patient's recipient jaw bone, while the optimal axial alignment of the prosthetic tooth tends to be dictated by the geometry of the patient's bite, lip support, phonetics and aesthetics. Thus, with current dental implants, the dental practitioner typically faces a choice of optimizing the orientation of the restoration for either (1) the implant seated in the bone, or (2) the prosthetic tooth extending into the mouth, or (3) some compromise in between. In any case, the result is generally a compromise of some sort.

OBJECTS OF THE INVENTION

Accordingly, one object of the present invention is to provide a novel dental implant which avoids the problems associated with the prior art.

Another object of the present invention is to provide a novel method for effecting a dental restoration.

SUMMARY OF THE INVENTION

These and other objects are addressed by the present invention, which comprises a novel dental implant system and a novel method for effecting a dental restoration using the same.

In one preferred form of the invention, the dental implant system comprises an implant fixture adapted to be deployed in a bone; an impression coping adapted to be selectively deployed on the implant fixture and in a dental impression; a laboratory analog adapted to be selectively deployed on the impression coping and in a dental cast; a spherical abutment adapted to be selectively deployed on the laboratory analog; and a multiaxis abutment adapted to be adjustably deployed on the spherical abutment.

And in one preferred form of the invention, the method for effecting a dental restoration comprises:

providing a dental implant system comprising:
  an implant fixture adapted to be deployed in a bone;
  an impression coping adapted to be selectively deployed on the implant fixture and in a dental impression;
  a laboratory analog adapted to be selectively deployed on the impression coping and in a dental cast;
  a spherical abutment adapted to be selectively deployed on the laboratory analog; and
  a multiaxis abutment adapted to be adjustably deployed on the spherical abutment;

positioning the implant fixture in the bone;
positioning the impression coping on the implant fixture;
making a dental impression of the impression coping and the surrounding portions of the patient's mouth;
removing the dental impression, with the impression coping attached thereto, from the patient's mouth;
positioning the laboratory analog on the impression coping;
making a cast of the laboratory analog and a portion of the impression coping;
removing the dental impression from the impression coping;
removing the impression coping from the laboratory analog;
positioning the spherical abutment on the laboratory analog;
positioning the multiaxis abutment on the spherical abutment and angling the multiaxis abutment atop the spherical abutment to the extent required for the dental restoration;
securing the multiaxis abutment in its angled position atop the spherical abutment;
generating a permanent abutment from the combined spherical abutment/multiaxis abutment, preferably through a so-called "lost wax/plastic technique" well known in the dental arts;
positioning the permanent abutment on the laboratory analog;
generating a prosthetic tooth for the permanent abutment; and
removing the permanent abutment from the laboratory analog and positioning the permanent abutment on the implant fixture.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein:

FIG. 3 is a schematic side view, partially in section, showing the impression coping in a dental impression, and with the dental implant system's laboratory analog mounted on the impression coping;

FIG. 4 is a schematic side view, partially in section, showing the laboratory analog incorporated in a dental cast, and with the dental implant system's spherical abutment mounted on the laboratory analog, and with the dental implant system's multiaxis abutment mounted on the spherical abutment;

FIGS. 7–11 show further details regarding the construction of the implant fixture;

FIGS. 12 and 13 show further details regarding the construction of the cover screw;

FIGS. 14–16 show further details regarding the construction of the impression coping;

FIGS. 27–46 show a preferred method for effecting a dental restoration using the dental implant system of the present invention;

FIGS. 47 and 48 show an abutment blank which may be machined down so as to form the permanent abutment shown in FIG. 5;

FIG. 49 shows one way of machining down the abutment blank of FIGS. 47 and 48 so as to form the permanent abutment shown in FIG. 5; and FIG. 50 shows another way of machining down the abutment blank of FIGS. 47 and 48 so as to form the permanent abutment shown in FIG. 5.

DETAILED DESCRIPTION OF THE PREFERRED EMBODIMENTS

The present invention generally comprises a dental implant system and a method for effecting a dental restoration using the same.

Figure 2:
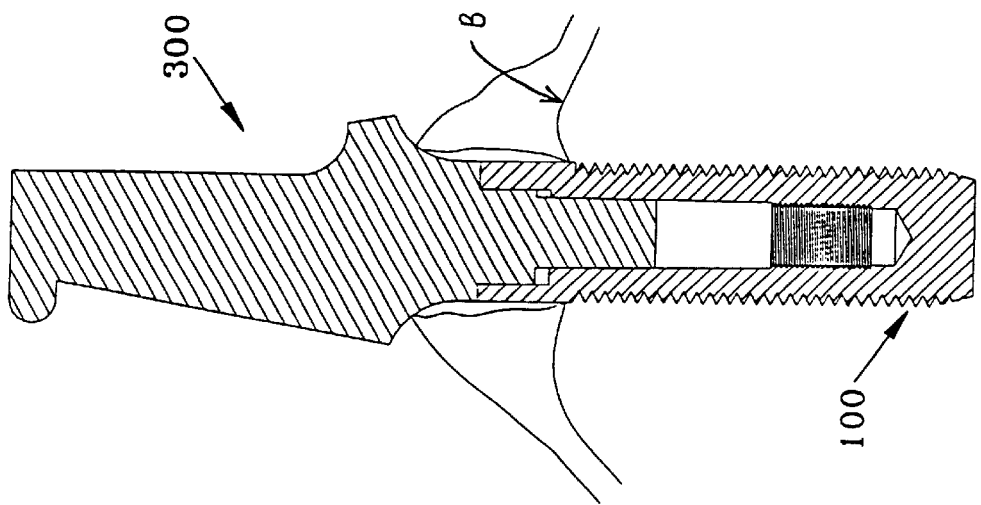
FIG. 2 is a schematic side view, partially in section, showing the dental implant system's impression coping mounting on the implant fixture.
Figure 1:
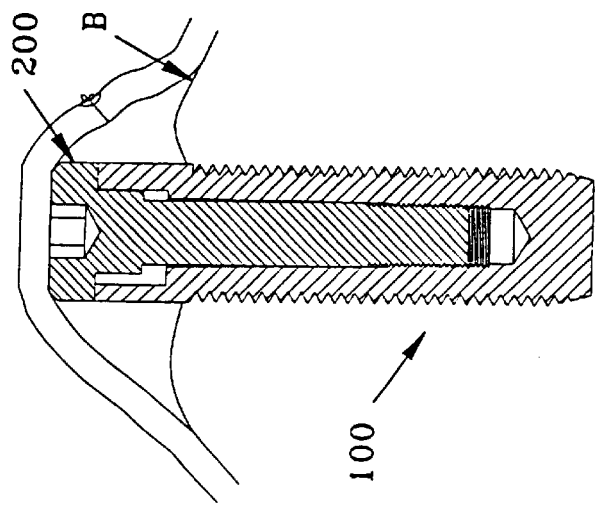
FIG. 1 is a schematic side view, partially in section, showing the dental implant system's implant fixture mounted in a jaw bone, and with the dental implant system's cover screw mounted in the implant fixture.
Figure 6:
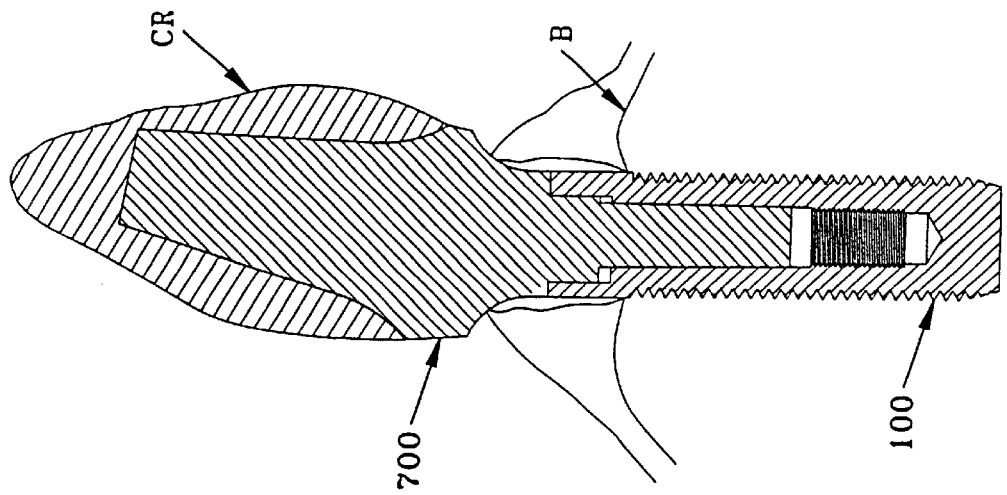
FIG. 6 is a schematic side view, partially in section, showing the implant fixture mounted in a jaw bone, the permanent abutment mounted on the implant fixture, and a prosthetic tooth mounted on the permanent abutment.
Figure 5:
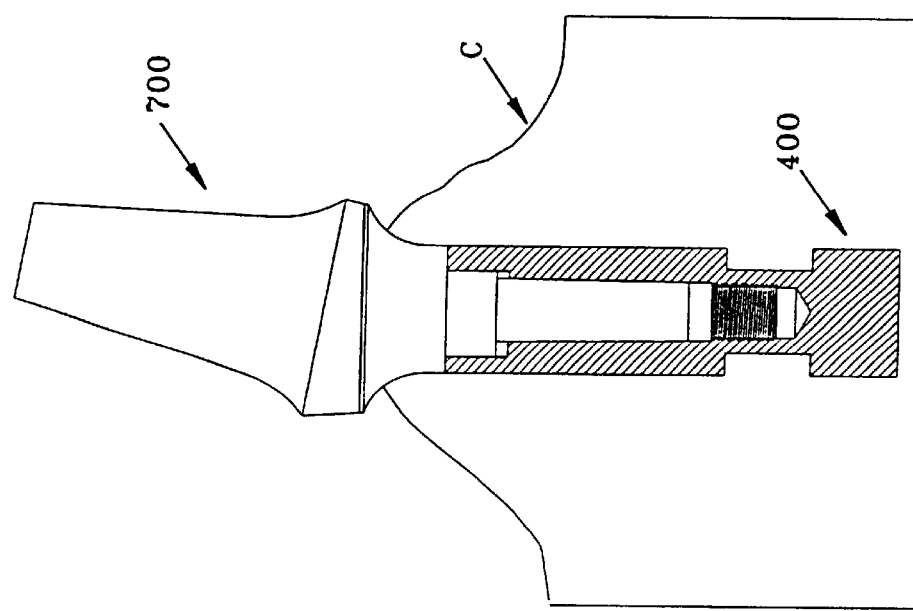
FIG. 5 is a schematic side view, partially in section, showing the laboratory analog incorporated in the dental cast, and with the dental implant system's permanent abutment mounted on the laboratory analog.
Figure 18:
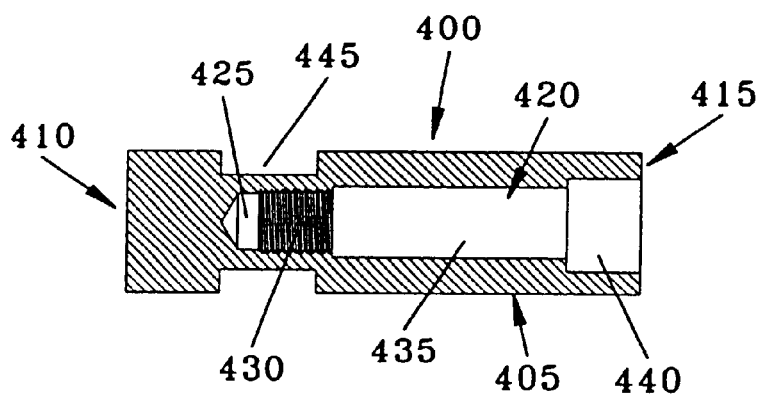
FIGS. 17–20 show further details regarding the construction of the laboratory analog.
Figures 17, 20:
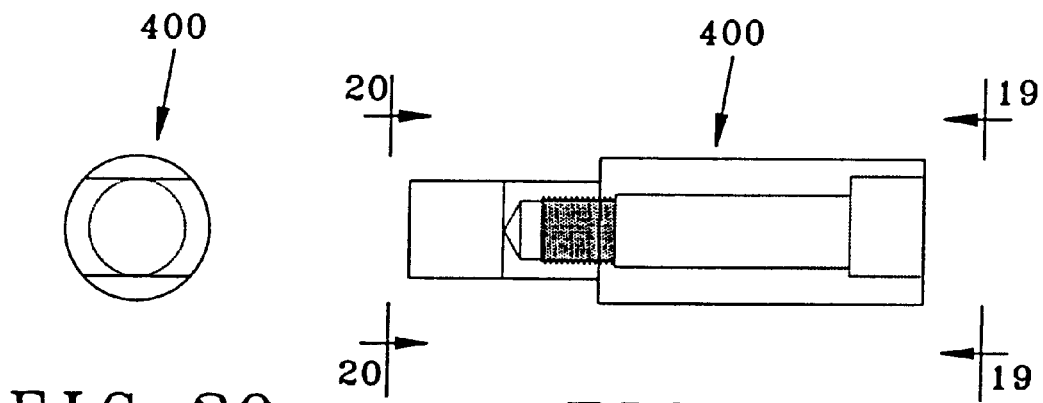
Figure 19:
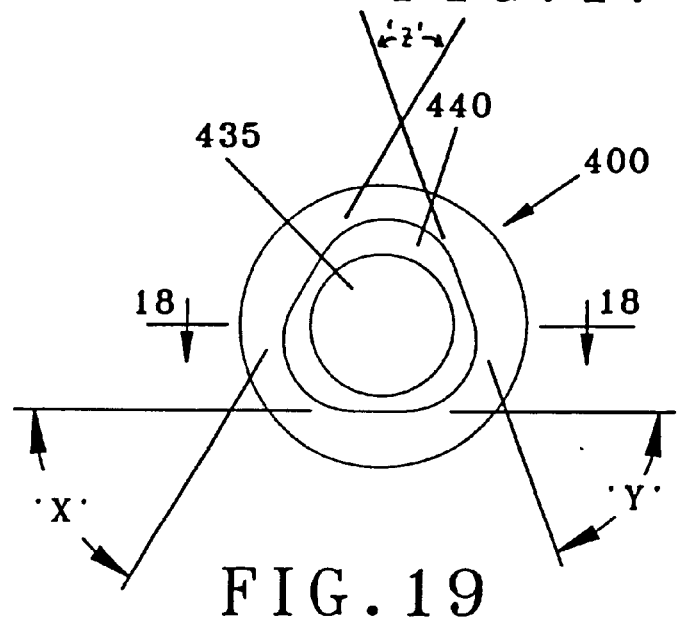

The dental implant system generally comprises an implant fixture 100 adapted to be deployed in a bone B (FIG. 1); a cover screw 200 adapted to be selectively deployed in implant fixture 100 (FIG. 1); an impression coping 300 adapted to be selectively deployed on implant fixture 100 (FIG. 2) and in a dental impression I (FIG. 3); a laboratory analog 400 adapted to be selectively deployed on impression coping 300 (FIG. 3) and in a dental cast C (FIG. 4); a spherical abutment 500 adapted to be selectively deployed on laboratory analog 400 (FIG. 4); and a multiaxis abutment 600 adapted to be adjustably deployed on spherical abutment 500 (FIG. 4). In accordance with the present invention, spherical abutment 500 and multiaxis abutment 600 may be used to generate a permanent abutment 700 which may be received by laboratory analog 400 (FIG. 5) and implant fixture 100 (FIG. 6). Permanent abutment 700 is adapted to receive a prosthetic tooth CR (FIG. 6), as will hereinafter be discussed in further detail.

Looking next at FIGS. 7–11, implant fixture 100 comprises a body 105 having a distal end 110 and a proximal end 115. A screw thread 120 extends from distal end 110 toward proximal end 115, but preferably terminates short of the proximal end surface 121 of proximal end 115. At least one cutting flute 125 is formed at the distal end of body 105. In the preferred embodiment, four such cutting flutes 125 are provided (FIG. 10). A multi-stage bore 130 extends distally from the proximal end surface 121 of body 105. Multi-stage bore 130 comprises a distalmost portion 135, a threaded portion 140, a tapered portion 150, and a proximalmost portion 155. Tapered portion 150 is tapered so as to form a so-called "Morse'a taper". The proximalmost portion 155 of bore 130 has an asymmetrical cross-section. In the preferred form of the invention, the proximalmost portion 155 of bore 130 has a generally asymmetrical triangular cross-section (FIG. 11). More particularly, and referring now to FIG. 11, in the preferred form of the invention the proximalmost portion 155 of bore 130 is formed so that angle X=angle Y≠angle Z. The three corners of triangular proximalmost portion 155 are preferably rounded so as to preserve as much material (and hence strength) as possible for body 105. This construction feature is important, inasmuch a body 105 may have a maximum outside diameter of less than 3 mm, i.e., in one preferred form of the invention, body 105 has a maximum outside diameter of only about 2.5 mm. This is approximately 30% smaller than the smallest existing dental implants.

Looking next at FIGS. 12 and 13, cover screw 200 comprises a shaft 205 and a head 210. Shaft 205 comprises a threaded distal portion 215, a first cylindrical portion 220, and a second cylindrical portion 225. Second cylindrical portion 225 is sized so that it may be turningly received in the implant fixture's proximalmost portion 155. Head 210 comprises an enlarged flange, and includes a hexagonal bore 230 extending distally into cover screw 200. Hexagonal bore 230 is adapted to receive an appropriately configured driver (not shown), by which cover screw 200 may be turned.

Looking next at FIGS. 14–16, impression coping 300 comprises a shaft 305, an asymmetrical portion 310 and a head 315. Asymmetrical portion 310 has a cross-sectional configuration which matches the cross-sectional configuration of the implant fixture's proximalmost portion 155, i.e., in the preferred form of the invention asymmetrical portion 310 has a generally triangular cross-section characterized by the aforementioned angles X, Y and Z. Head 315 also, preferably, has an asymmetrical shape characterized by a surface 320 and an end rim 321, in order to facilitate securing the impression coping in a dental impression I (FIG. 3), as will hereinafter be discussed in further detail.

Looking next at FIGS. 17–20, laboratory analog 400 comprises a body 405 having a first end 410 and a second end 415. A multistage bore 420 extends from the body's second end 415 towards the body's first end 410. Multistage bore 420 comprises a deepest portion 425, a threaded portion 430, an elongated portion 435, and a shallowest portion 440. The shallowest portion 440 of bore 420 has an asymmetrical cross-section (FIG. 19) which matches the cross-sectional configuration of the impression coping's asymmetrical portion 310, i.e., in the preferred form of the invention, shallowest portion 440 has a generally triangular cross-section characterized by the aforementioned angles X, Y and Z. Preferably, the exterior surface of laboratory analog 400 is grooved or notched as shown at 445 (FIG. 18) in order to facilitate securing the laboratory analog in a dental cast C (FIGS. 4 and 5), as will hereinafter be discussed in further detail.

Figures 21, 22:
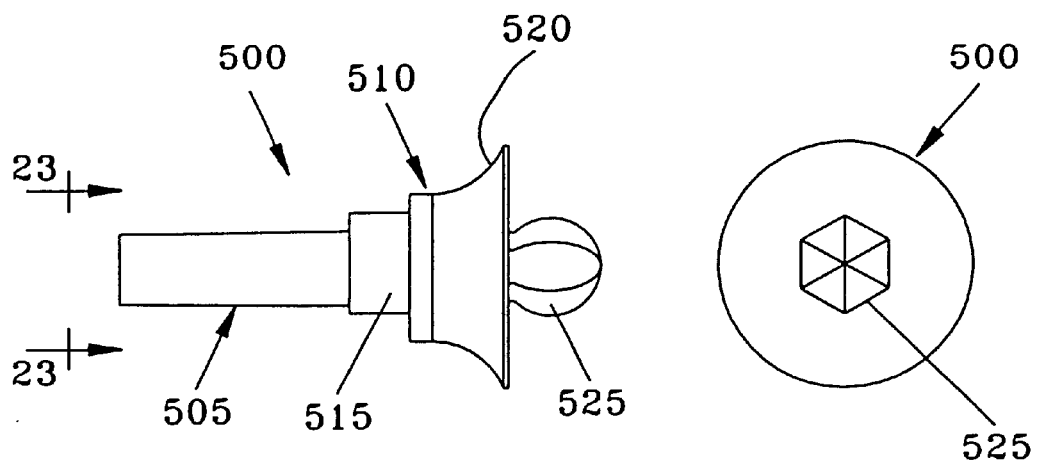
FIGS. 21–23 show further details regarding the construction of the spherical abutment.
Figure 23:
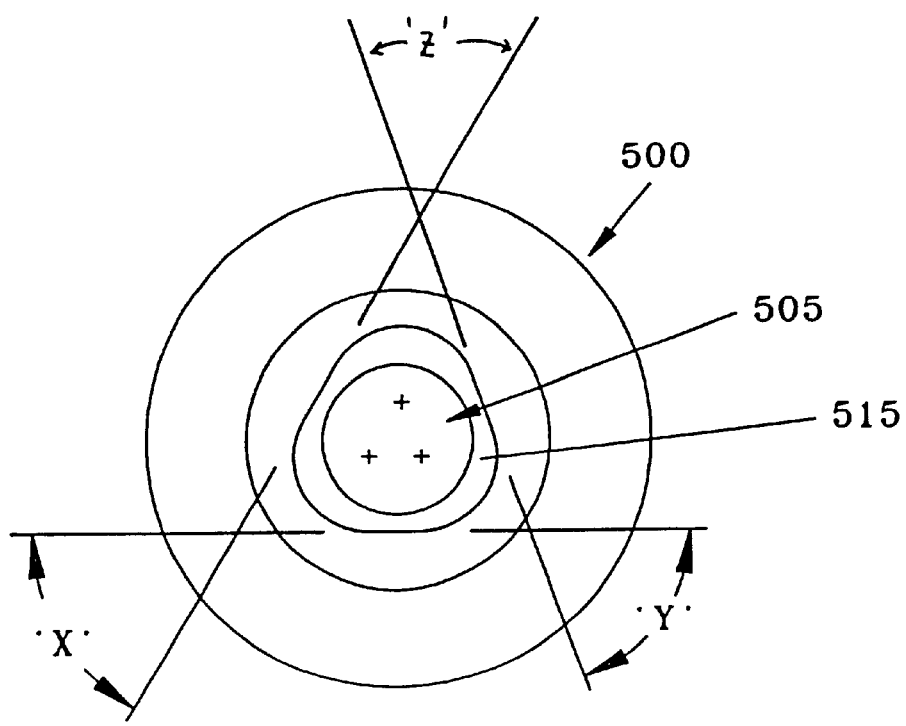

Looking next at FIGS. 21–23, spherical abutment 500 generally comprises a shaft 505 and a head 510. Head 510 in turn generally comprises a distalmost section 515 having an asymmetrical cross-section (FIG. 23) which matches the cross-sectional configurations of the laboratory analog's shallowest portion 440 and the implant fixture's proximal-most portion 155, i.e., in the preferred embodiment, distal-most section 515 has a generally triangular cross-section characterized by the aforementioned angles X, Y and Z. The spherical abutment's head 510 also comprises an outwardly-tapering section 520, and a hex-shaped ball 525.

Figure 25:
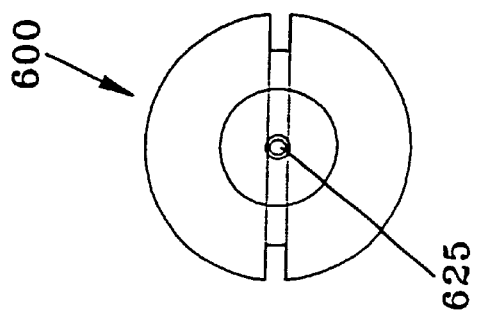
FIGS. 24–26 show further details regarding the construction of the multiaxis abutment.
Figure 24:
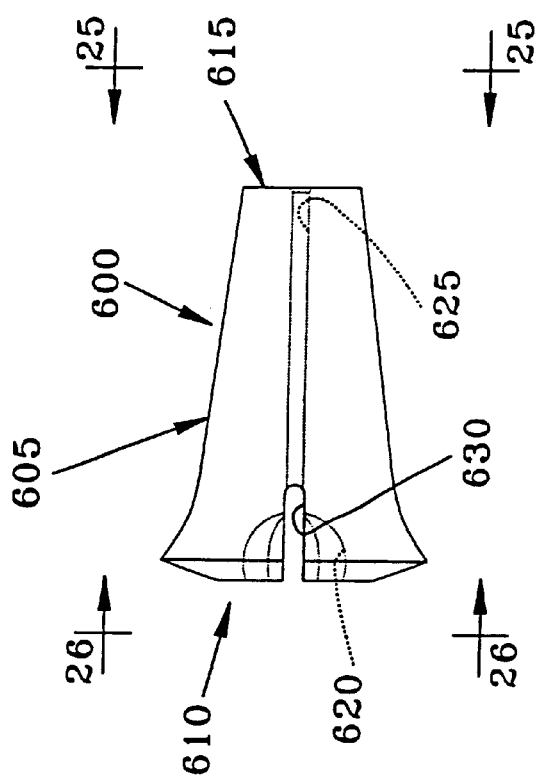
Figure 26:
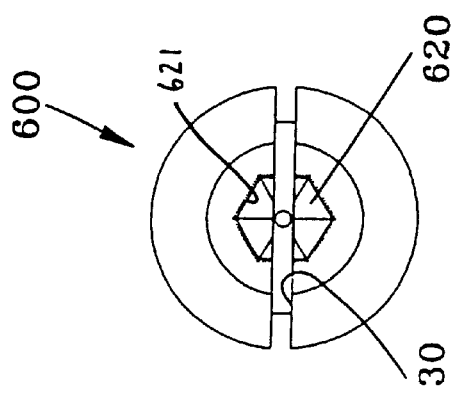

Looking next at FIGS. 24–26, multiaxis abutment 600 comprises a body 605 having a distal end 610 and a proximal end 615. A hex-shaped ball recess 620 opens on distal end 610. Hex-shaped ball recess 620 corresponds to the shape of the spherical abutment's hex-shaped ball 525, in order that ball 525 may be received in recess 620. The distalmost portion of recess 620 is characterized by a hex-shaped rim 621. It should be appreciated that the diameter across opposing faces of hex-shaped rim 621 is less than the maximum diameter across corresponding surfaces of hex-shaped ball 525; as a result of this construction, rim 621 must expand slightly in order for recess 620 to receive ball 525, but rim 621 will thereafter keep the ball 525 secured in recess 620. A central passageway 625 opens on proximal end 615 and extends through body 605 so as to join hex-shaped ball recess 620. A diametrically-extending groove 630 extends across the distal end 610 of body 605. Groove 630 permits the distal end of body 605 (i.e., rim 621) to elastically expand to the extent necessary for ball 525 to snap into recess 620.

In one preferred form of the invention, the dental implant system is used as follows.

First, the patient's gingiva G is surgically opened (FIG. 27) and the underlying bone B exposed. Then implant fixture 100 is positioned in bone B. Preferably this is done by first drilling a hole into bone B and then screwing implant fixture 100 into the hole, with the implant fixture's cutting flutes 125 further opening the bone and with screw threads 120 securely engaging the bone. In accordance with the present invention, implant fixture 100 is positioned in bone B so as to substantially optimize seating of implant fixture 100 in bone B, and substantially without concern for the optimal axial alignment of the prosthetic tooth which will ultimately extend into the patient's mouth.

Then cover screw 200 is screwed into implant fixture 100 so as to close off the open proximal end of the implant fixture (FIGS. 27 and 28). As this occurs, the cover screw's distal threads 215 will engage the implant fixture's screw threads 140, and the cover screw's cylindrical portion 225 is received in the implant fixture's bore portion 155. The cover screw's hexagonal bore 230 may be used to turn the cover screw down into the implant fixture.

Next, the gingiva G is sutured closed over the assembled implant fixture 100 and cover screw 200 (FIG. 28).

The apparatus is then preferably left in this position until osseo-integration has been effected between implant fixture 100 and bone B.

Next, implant fixture 100 and cover screw 200 are exposed, and cover screw 200 is removed (FIG. 29).

Figures 30, 31, 32:
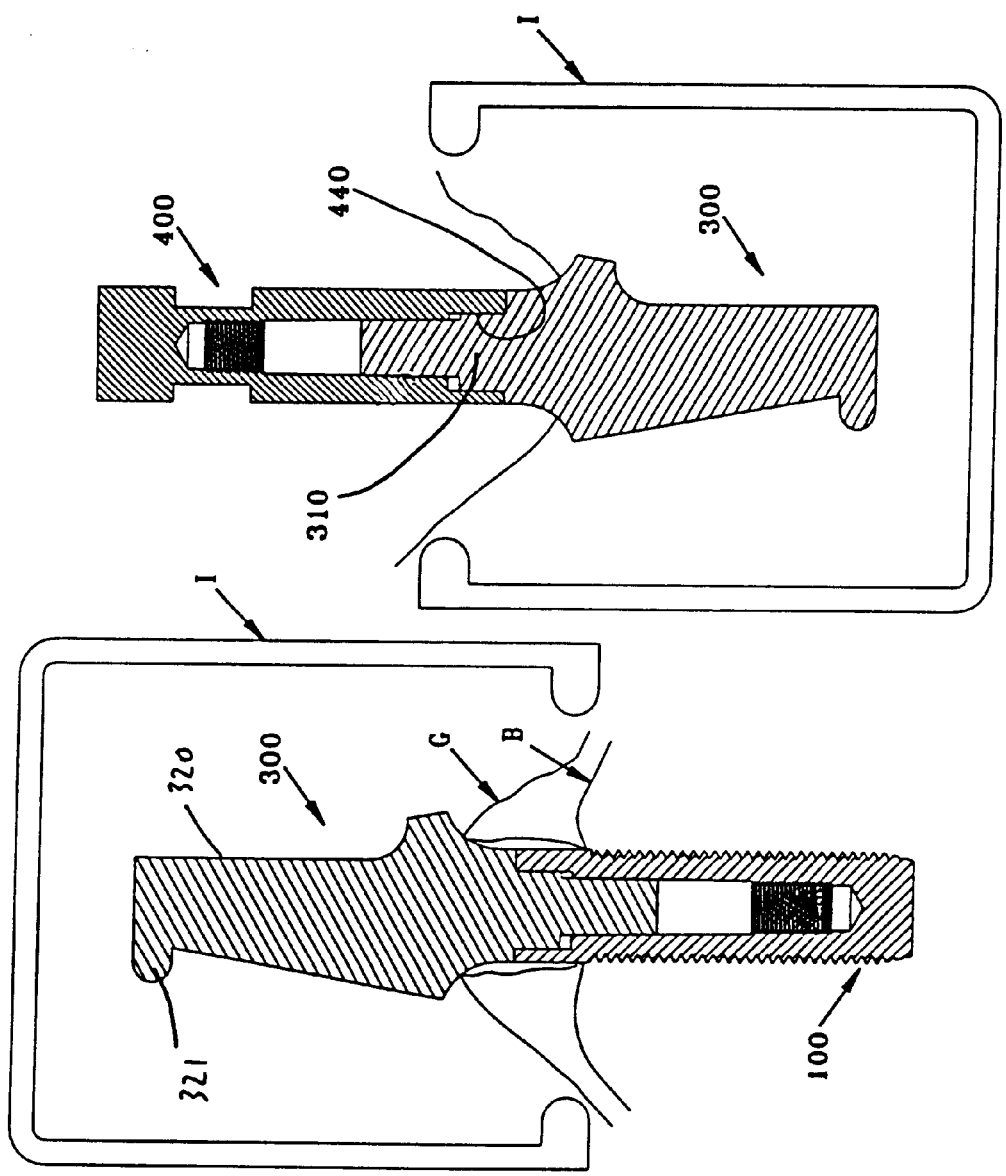

Then, impression coping 300 is mounted in implant fixture 100 (FIG. 30). It should be appreciated that, as this occurs, the triangular cross-section of the implant fixture's bore portion 155, and the triangular cross-section of the impression coping's triangular portion 310, will mate with one another so as to fix the orientation of impression coping 300 relative to implant fixture 100.

Next, a dental impression I is made of the patient's mouth, using conventional dental impression apparatus (FIG. 31).

Then dental impression I, with impression coping 300 attached thereto, is removed from the patient's mouth. In this respect it will be appreciated that the particular surface profile (e.g., surface 320 and rim 321) of impression coping 300 will help retain the impression coping 300 in dental impression I.

Next, dental impression I, with impression coping 300 attached thereto, is inverted, and laboratory analog 400 is fit over the exposed portion of impression coping 300 (FIG. 32). It should be appreciated that, as this occurs, the triangular cross-section of the impression coping's asymmetrical portion 310, and the triangular cross-section of the laboratory analog's bore portion 440, will mate with one another so as to fix the orientation of laboratory analog 400 relative to impression coping 300. In particular, it will be appreciated that impression coping 300 and laboratory analog 400 will have the same orientation relative to one another at this stage in the process that impression copying 300 and implant fixture 100 had at an earlier (see, for example, FIG. 30) stage of the process.

Then a dental cast C is poured (FIG. 33).

Next, dental cast C and dental impression I are inverted, and dental impression I is removed, leaving laboratory analog 400 embedded in dental cast C, and impression coping 300 protruding out of dental cast C (FIG. 34).

Then impression coping 300 is removed (FIG. 35).

At this point, a laboratory duplicate (i.e., dental cast C and laboratory analog 400) has effectively been created of the patient's mouth (i.e., bone B, gingiva G and implant fixture 100).

Next, spherical abutment 500 is placed in laboratory analog 400 (FIG. 36). It should be appreciated that, as this occurs, the triangular cross-section of the spherical abutment's asymmetrical section 515, and the triangular cross-section of the laboratory analog's bore portion 440, will mate with one another so as to fix the orientation of spherical abutment 500 relative to laboratory analog 400.

Then multiaxis abutment 600 is mounted on spherical abutment 500 (FIG. 37). This is done by snapping the bottom end of the multiaxis abutment onto the top end of the spherical abutment, i.e., by forcing the rim 621 of the multiaxis abutment over the spherical abutment's hex-shaped ball 525 so that the hex-shaped ball is seated in the multiaxis abutment's hex-shaped ball recess 620. It should be appreciated that, as this occurs, the multiaxis abutment's diametrically-extending groove 630 will permit the distal end of the multiaxis abutment to initially elastically expand to the extent required for mounting to occur; however, the distal end of multiaxis abutment 600 will then return to its original dimensions so as to thereafter movably capture the multiaxis abutment to the proximal end of spherical abutment 500. In particular, the mating hexagonal shapes of the spherical abutment's hex-shaped ball 525 and the multiaxis abutment's hex-shaped ball recess 620 will permit the multiaxis abutment 600 to pivot about the longitudinal axis 530 (FIG. 38) of spherical abutment 500, but will prevent the multiaxis abutment from rotating about its own longitudinal axis.

Next, multiaxis abutment 600 is angled atop spherical abutment 500 (FIG. 38) to the extent required for the dental restoration. In particular, multiaxis abutment 600 is angled atop spherical abutment 500 so that the longitudinal axis of the multiaxis abutment is aligned with the optimal axial alignment for the prosthetic tooth which will ultimately extend into the patient's mouth.

Figure 39:
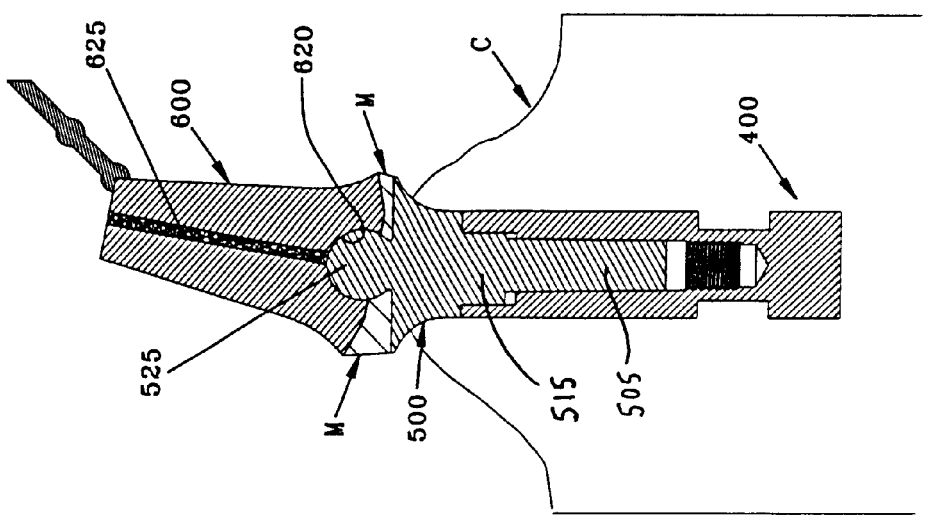

Next, multiaxis abutment 600 is fixed in place atop spherical abutment 500 (FIG. 39). This may be done by flowing adhesive down the multiaxis abutment's central passageway 625 so that the adhesive fills the space between the spherical abutment's hex-shaped ball 525 and the multiaxis abutment's hex-shaped ball recess 620. This adhesive also seals the multiaxis abutment's central passageway 625. In addition, additional material M (FIG. 39) may be used to fill the gap between the top of spherical abutment 500 and the bottom of multiaxis abutment 600, as well as the multiaxis abutment's diametrically-extending groove 630. Material M may comprise one or more wax or plastic materials of the sort well known in the dental arts.

Figure 40:
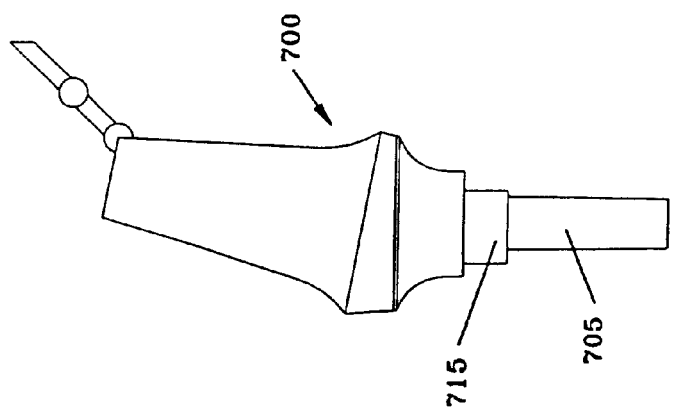

The combined spherical abutment 500/multiaxis abutment 600, having been fixed in position relative to one another, are then removed from dental cast C and fabricated in permanent form (e.g., out of metal) so as to form a corresponding permanent abutment 700 (FIG. 40). By way of example but not limitation, the combined spherical abutment 500/multiaxis abutment 600 can be cast, using a so-called "lost wax/plastic technique" well known in the dental arts, so as to form the corresponding permanent abutment 700. Permanent abutment 700 will include, among other things, a triangular portion 715 (corresponding to the triangular cross-section of the spherical abutment's triangular portion 515) and a shaft 705 (corresponding to the spherical abutment's shaft 505).

Figure 41:
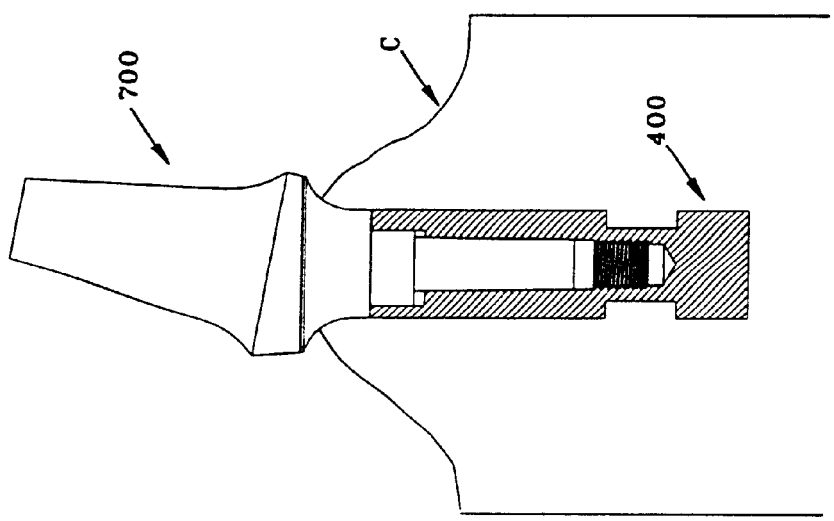

At this point, the permanent abutment 700 can be positioned on the laboratory analog 400 mounted in dental cast C (FIG. 41). In this respect it will be appreciated that when permanent abutment 700 is positioned on laboratory analog 400, the asymmetrical cross-section of the permanent abutment's triangular portion 715 will coordinate with the asymmetrical cross-section of the laboratory analog's triangular bore 440 so as to cause permanent abutment 700 to assume exactly the same orientation on the laboratory analog at this stage in the procedure that the combined spherical abutment 500/multiaxis abutment 600 assumed earlier in the procedure (FIG. 39). Once permanent abutment 700 has been mounted on laboratory analog 400, an appropriate prosthetic tooth CR (FIG. 42) can be fabricated.

Then prosthetic tooth CR may be test mounted on the permanent abutment 700 mounted on dental cast C (FIG. 43).

Once the dental practitioner is certain that permanent abutment 700 and prosthetic tooth CR are ready to be mounted in the patient, implant fixture 100 (which is positioned in the patient's bone B) is re-exposed, if it is not still exposed (FIG. 44).

Figure 45:
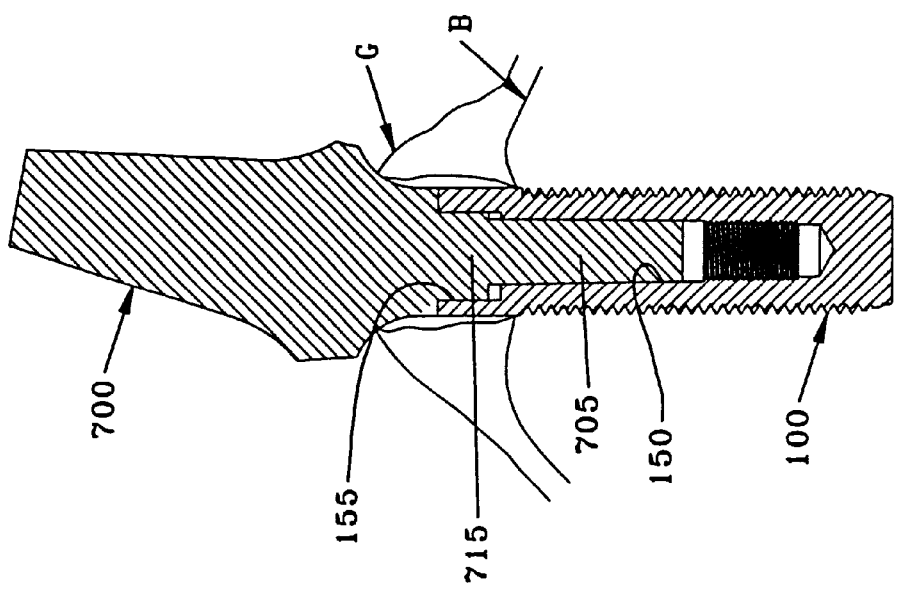

Then permanent abutment 700 is mounted on implant fixture 100 (FIG. 45). It will be appreciated that, as this occurs, the triangular cross-section of the permanent abutment's triangular portion 715 (FIG. 45), and the triangular cross-section of the implant fixture's triangular bore portion 155, will mate with one another so as to fix the orientation of permanent abutment 700 relative to implant fixture 700. In particular, permanent abutment 700 will assume precisely the same orientation with respect to implant fixture 100 that permanent abutment 700 previously assumed with respect to laboratory analog 400 (compare, for example, FIG. 45 with FIG. 41). At the same time, insertion of the permanent abutment's shaft 705 (FIG. 45) into the implant fixture's tapered portion 150 will cause permanent abutment 700 to lock itself to implant fixture 100, due to the "Morse'a taper" established by the implant fixture's tapered portion 150. If desired, this mechanical interlock may also be enhanced by placing a suitable adhesive into the implant fixture's bore 130 before inserting the permanent abutment's shaft 705 therein. Alternatively, the "Morse'a taper" may be omitted entirely from implant fixture 100, and only adhesive used to secure permanent abutment 700 to implant fixture 100.

Figure 46:
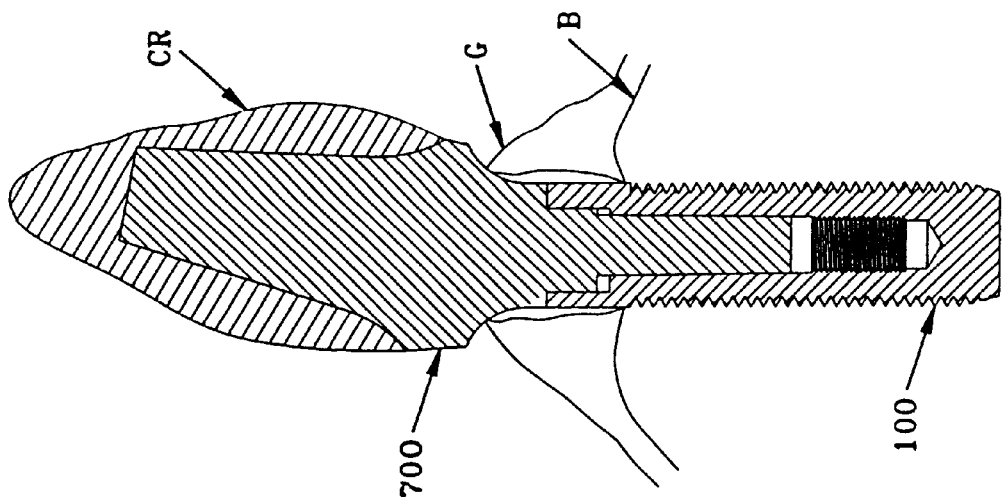

In any case, once permanent abutment 700 has been secured in implant fixture 100, prosthetic tooth CR may be secured onto the proximal end of permanent abutment 700 (FIG. 46) using conventional dental adhesive. This will effectively complete the dental restoration.

MODIFICATIONS OF THE PREFERRED EMBODIMENTS

Numerous modifications may be made to the preferred embodiments discussed above without departing from the scope of the present invention.

For example, permanent abutment 700 need not necessarily be made by casting from the combined spherical abutment 500/multiaxis abutment 600. Rather, permanent abutment 700 can be made by a machining process. More particularly, and looking now at FIGS. 47–50, a permanent abutment 700 can be formed by machining an abutment blank AB (FIGS. 47 and 48) into the permanent abutment 700. Such machining may be done in numerous ways well known to those skilled in the art. By way of example but not limitation, FIG. 49 shows permanent abutment 700 being formed by an automated machining process; FIG. 50 shows permanent abutment 700 being formed by a manual machining process.

And one might attach prosthetic tooth CR to permanent abutment 700 prior to positioning the permanent abutment in implant fixture 100, rather than after positioning in implant fixture 100 as disclosed above.

By way of further example but not limitation, one might also omit permanent abutment 700 altogether and simply mount prosthetic tooth CR directly to the combined spherical abutment 500/multiaxis abutment 600 shown in FIG. 39, assuming that spherical abutment 500 and multiaxis abutment 600 are formed out of appropriate materials and have been suitably secured relative to one another.

Furthermore, the opposing surfaces of spherical abutment 500 and multiaxis abutment 600 may be etched and/or roughened so as to facilitate retention of material therebetween. In addition, the opposing surfaces of hex-shaped ball 525 and hex-shaped ball recess 620 may also be etched and/or roughened to facilitate retention of adhesive therebetween.

Still other modifications may be made to the preferred embodiments disclosed above without departing from the scope of the present invention.

ADVANTAGES OF THE INVENTION

Numerous advantages are achieved by the provision and use of the present invention.

For one thing, the present invention provides a novel dental implant which avoids the problems associated with the prior art.

And the present invention provides a novel method for effecting a dental restoration.

What is claimed is:

1. A method for effecting a dental restoration, said method comprising:
   providing a dental implant system comprising:
   an implant fixture adapted to be deployed in a bone;
   an impression coping adapted to be selectively deployed on said implant fixture and in a dental impression;
   a laboratory analog adapted to be selectively deployed on said impression coping and in a dental cast;
   a spherical abutment adapted to be selectively deployed on said laboratory analog; and
   a multiaxis abutment adapted to be adjustably deployed on said spherical abutment;
   positioning said implant fixture in said bone;
   positioning said impression coping on said implant fixture;
   making a dental impression of said impression coping and the surrounding portions of the patient's mouth;
   removing the dental impression, with said impression coping attached thereto, from the patient's mouth;
   positioning said laboratory analog on said impression coping;
   making a cast of said laboratory analog and a portion of said impression coping;
   removing the dental impression from said impression coping;
   removing said impression coping from said laboratory analog;
   positioning said spherical abutment in said laboratory analog;
   positioning said multiaxis abutment on said spherical abutment and angling said multiaxis abutment atop said spherical abutment to the extent required for the dental restoration;
   securing said multiaxis abutment in its angled position atop said spherical abutment;
   generating a permanent abutment from the combined spherical abutment/multiaxis abutment;
   positioning said permanent abutment in said laboratory analog;
   generating a prosthetic tooth for said permanent abutment; and
   removing said permanent abutment from said laboratory analog and positioning said permanent abutment on said implant fixture.

2. An implant fixture having a proximal end and a distal end, said proximal end of said implant fixture containing an asymmetrical bore, and an impression coping having a proximal end and a distal end, said distal end of said impression coping having an asymmetrical portion, with said asymmetrical bore of said implant fixture being configured to receive said asymmetrical portion of said impression coping in a single predetermined orientation.

3. An implant fixture according to claim 2 wherein said implant fixture has a bore, said implant fixture being adapted to mate with a cover screw for sealing said bore.

4. An implant fixture according to claim 2 wherein said implant fixture has flutes for cutting bone.

5. An implant fixture according to claim 2 wherein said implant fixture has threads for securing said implant fixture to bone.

6. An implant fixture according to claim 2 wherein said implant fixture includes a distal end with an exterior taper.

7. An implant fixture having a proximal end and a distal end, said proximal end of said implant fixture containing an asymmetrical bore, and an abutment having a proximal end and a distal end, said distal end of said abutment having an asymmetrical portion, with said asymmetrical bore of said implant fixture being configured to receive said asymmetrical portion of said abutment in a single predetermined orientation.

8. An implant fixture according to claim 7 wherein said implant fixture has a bore configured to receive the abutment, said implant fixture and the abutment being configured to mate when said implant fixture and the abutment are positioned with said predetermined orientation.

9. An implant fixture according to claim 8 wherein a portion of said bore comprises a "Morse'a taper".

10. An implant fixture according to claim 7 wherein said abutment comprises a hex-shaped ball.

11. An implant fixture according to claim 7 wherein said abutment is permanent.

12. An impression coping having a proximal end and a distal end, said distal end of said impression coping having an asymmetrical portion, and an implant fixture having a proximal end and a distal end, said proximal end of said implant fixture containing an asymmetrical bore, with said asymmetrical bore of said implant fixture being configured to receive said asymmetrical portion of said impression coping in a single predetermined orientation.

13. An impression coping according to claim 12 wherein said asymmetrical portion of said impression coping mates with a laboratory analog having a proximal end and a distal end, said proximal end of said laboratory analog containing an asymmetrical bore, whereby said asymmetrical bore of said laboratory analog is configured to receive said asymmetrical portion of said impression coping in a second single predetermined orientation.

14. A laboratory analog having a proximal end and a distal end, said proximal end of said laboratory analog containing an asymmetrical bore, and an impression coping having a proximal end and a distal end, said distal end of said impression coping having an asymmetrical portion, with said asymmetrical bore of said laboratory analog being configured to receive said asymmetrical portion of said impression coping in a single predetermined orientation.

15. A laboratory analog according to claim 14 wherein said laboratory analog is configured to be incorporated in a dental cast.

16. A laboratory analogue according to claim 14 wherein said laboratory analog has a notch for enhancing fixation of said laboratory analog in a dental cast.

17. An abutment having a proximal end and a distal end, said distal end of said abutment having an asymmetrical portion, and an implant fixture having a proximal end and a distal end, said proximal end of said implant fixture containing an asymmetrical bore, with said asymmetrical bore of said implant fixture being configured to receive said asymmetrical portion of said abutment in a single predetermined orientation.

18. An abutment according to claim 17 wherein said asymmetrical end of said abutment mates with a laboratory analog having a proximal end and a distal end, said proximal end of said laboratory analog containing an asymmetrical bore, whereby said asymmetrical bore is configured to receive said asymmetrical portion of said laboratory analog in a second single predetermined orientation.

19. An abutment according to claim 17 wherein said abutment comprises:
   a spherical abutment, receivable in the implant fixture; and a multiaxis abutment mounted on said spherical abutment.

20. An abutment according to claim 19 wherein one of said spherical abutment and said multiaxis abutment includes a head; and the other of spherical abutment and said multiaxis abutment has a socket configured to receive said head.

21. An abutment according to claim 20 wherein said head and said socket are configured so that said spherical abutment and said multiaxis abutment pivot, but do not rotate, relative to one another.

22. An abutment according to claim 20 wherein said head defines a hex-shaped ball; and wherein said socket defines a hex-shaped ball recess.

23. An abutment according to claim 20 wherein one of said spherical abutment and said multiaxis abutment has a passage for providing adhesive for fixing said head with respect to said socket.

24. An abutment according to claim 17 wherein said abutment is generated according to a modeled abutment.

25. An abutment according to claim 24 wherein said abutment is generated by casting or milling.

* * * * *